US00PP15471P3

(12) United States Plant Patent
Love

(10) Patent No.: US PP15,471 P3
(45) Date of Patent: Jan. 11, 2005

(54) ***LIRIOPE MUSCARI* PLANT NAMED 'LOVE POTION NO. 13'**

(50) Latin Name: *Liriope muscari*
Varietal Denomination: Love Potion No. 13

(76) Inventor: Ron Love, 13000 W. Highway 318, Williston, FL (US) 32696

( * ) Notice: Subject to any disclaimer, the term of this patent is extended or adjusted under 35 U.S.C. 154(b) by 0 days.

(21) Appl. No.: 10/224,141

(22) Filed: Aug. 19, 2002

(65) Prior Publication Data

US 2004/0034894 P1 Feb. 19, 2004

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Michelle Kizilkaya
(74) *Attorney, Agent, or Firm*—W. Dennis Drehkoff; Ladas & Parry

(57) ABSTRACT

A new and distinct variety of *Liriope muscari* characterized as to novelty by increased vigor, increased raceme length, inflorescence with increased duration, intensity, height and uniformity. The blooming period for the flower is earlier and longer than other varieties.

4 Drawing Sheets

Botanical classification: *Liriope muscari.*
Cultivar designation: 'Love Potion No. 13'.

BACKGROUND OF THE INVENTION

*Liriope muscari* Evergreen plant is a popular landscape plant grown in the southeastern United States because its dark green leaves and spikes of lavender-colored flowers require little maintenance.

It is used primarily in mass planting in front of shrubbery. 'Evergreen giant' has served well as a dark green grass-like groundcover for many years. However, it has been losing vigor and it is more susceptible to disease than in the past.

The new *Liriope* variety was discovered growing in a bed with about 20,000 'Evergreen giant' plants in the commercial nursery facilities of Rode Groundcovers, Inc. located near Williston, Fla. in the summer of 1997.

Propagation of the cultivar has been done asexually by division at the same location. Noteworthy characteristics of this new cultivar are shown in its floral display that has better duration, intensity, height and uniformity than other *Liriope* varieties available in the United States. Several generations of the new plant have been evaluated and the distinctive characteristics of the plant have remained stable.

SUMMARY OF THE INVENTION

The following are the most outstanding and distinguishing characteristics of this new cultivar when grown under normal horticultural conditions in Williston, Fla.

1. A floral display that has better duration, intensity, height and uniformity than other *Liriope* varieties in the marketplace.
2. A rate of multiplication, using ordinary nursery methods, that is twice as fast as Evergreen giant.
3. A leaf blade that is wider than other large *Liriope* varieties.
4. A leaf that is pendulous and thus more revealing of the flower raceme.

5. Flower racemes are longer, more uniform and stouter than other large *Liriope* varieties.
6. Unopened flower buds are violet not white as in other large *Liriope* varieties and thus have more visual impact.
7. Flower bundles along the length of the raceme are much closer together and more uniform in spacing.
8. Blooms earlier than other large *Liriope* varieties (June 15$^{th}$ to September 1$^{st}$ peaking around July 15$^{th}$).
9. The number of flower bundles along the flower raceme is approximately two times as many as other *Liriope* varieties.
10. The color of the individual bloom is a darker violet than other large *'Liriope'* and has a stronger visual impact above the foliage.
11. The height at maturity is 18–24".
12. Grows well in sun or shade.
13. Uniformity in mass plantings is excellent.
14. 'Love Potion #13' has good drought tolerance.
15. It has good cold tolerance and is hardy in zones 8B through 11.
16. Individual divisions or bibs have significantly more leaves per fan and more leaf surface area than other large *Liriope* varieties.
17. 'Love Potion #13' exhibits good resistance to common fungal and bacterial plant pathogens.
18. Increased plant vigor and the amount of leaves per division result in greatly reduced finishing times in a commercial nursery.
19. Remains dark green throughout the winter and does not exhibit "leaf scorch" after frosting.
20. Each division blooms.

DESCRIPTION OF THE DRAWINGS

The new *Liriope muscari* variety is illustrated by the accompanying photographic prints in which.

BOTANICAL DESCRIPTION OF THE PLANT

Figure 1:
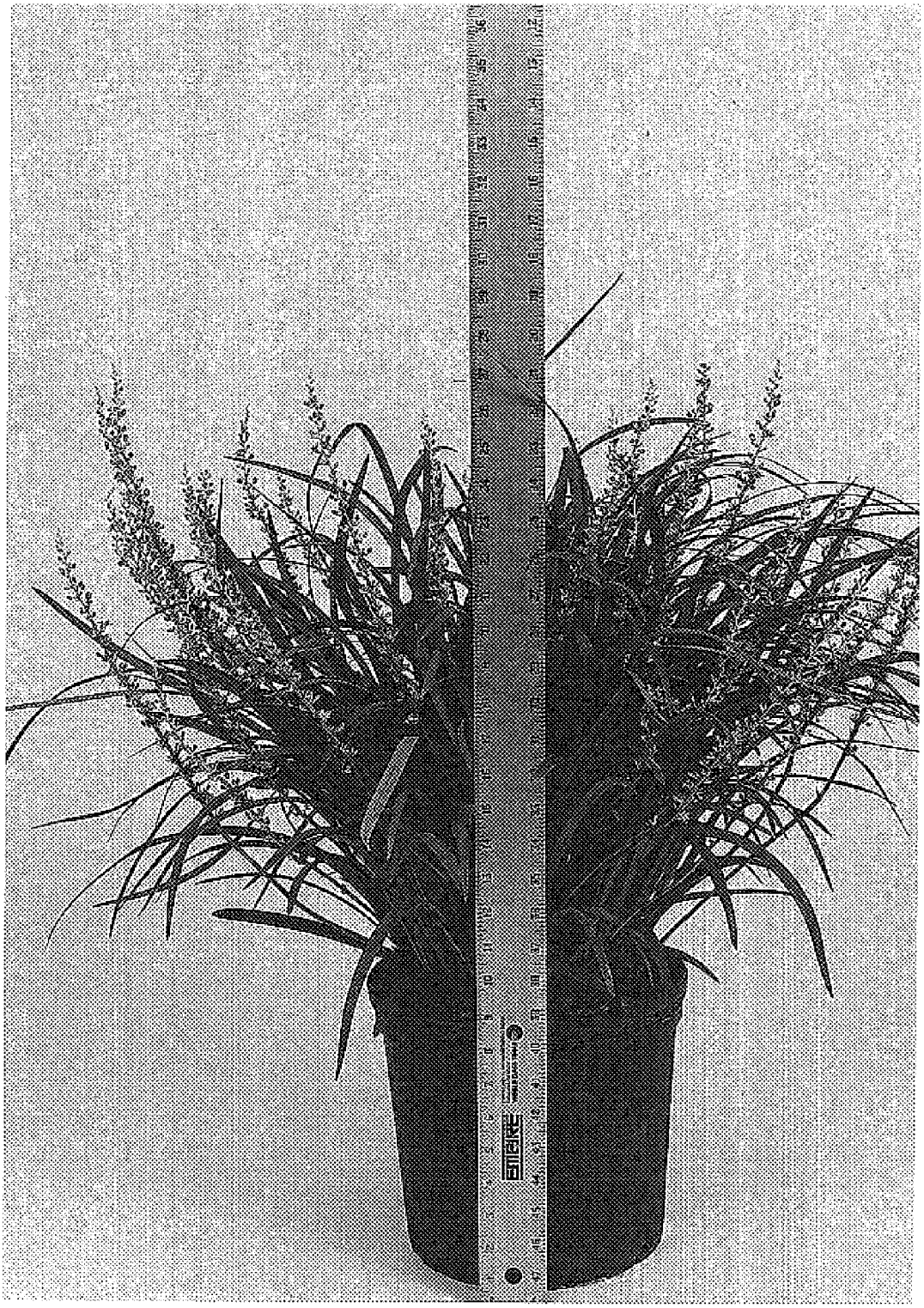
FIG. 1 is a photograph of the new variety 'Love Potion #13' showing long flower racemes which are uniform and stouter than other *Liriope* plants and the dark green color of the grass-like foliage.
Figure 2:
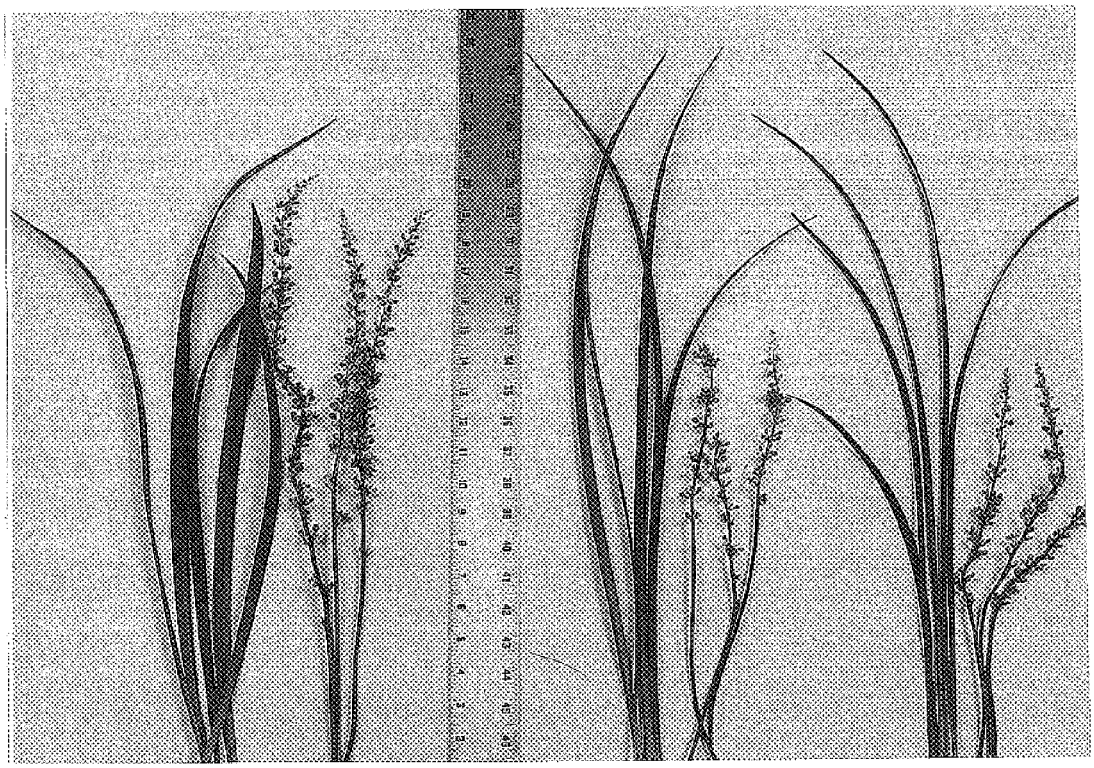
FIG. 2 is a side-by-side photograph of the cultivar of the present invention shown on the left side, Evergreen giant in the middle, and the variety 'Merton Jacobs', the subject of U.S. Plant Pat. No. 12,068 on the right. The photograph shows the large number of flowers on the flower racemes of the new cultivar that approximate by twice the normal flowers of the other two varieties.
Figure 3:
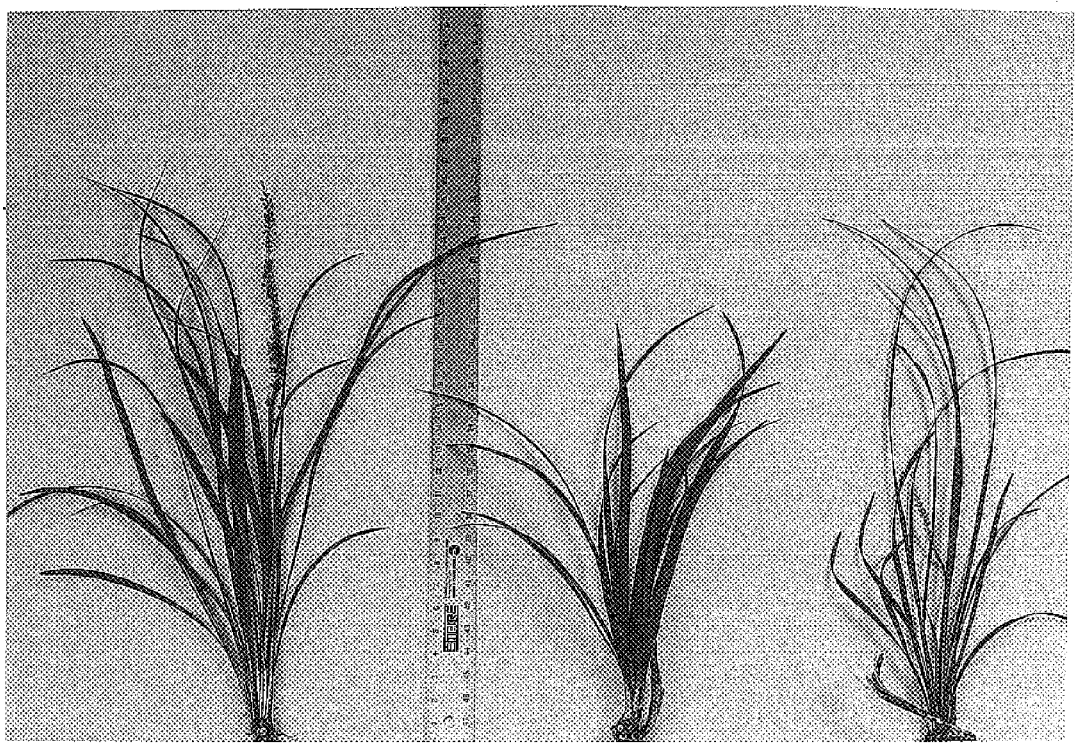
FIG. 3 shows a side-by-side photograph of the new cultivar, Evergreen giant and the variety 'Merton Jacobs'. All plant material has been divided and ready for planting.
Figure 4:
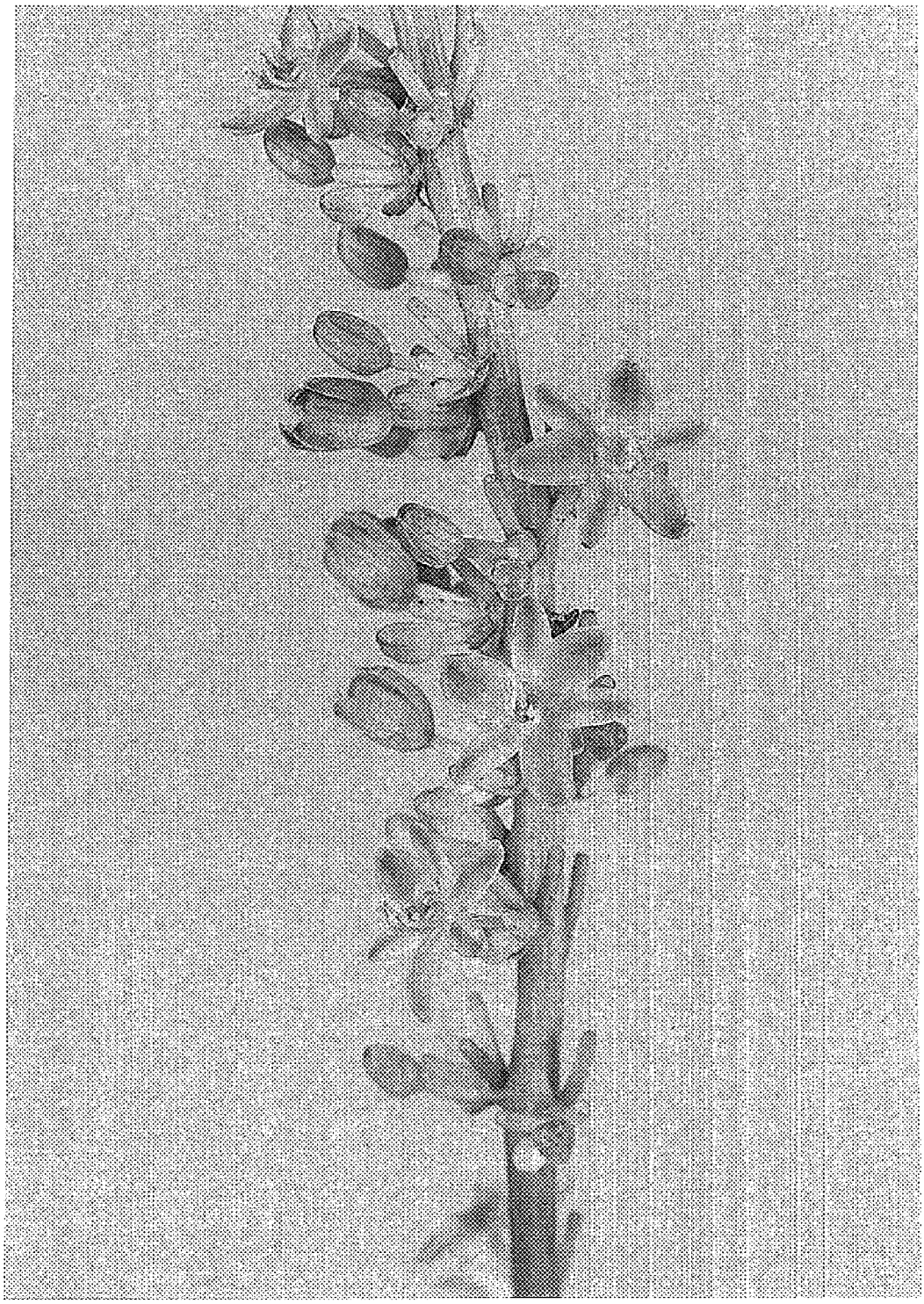
FIG. 4 shows a close-up photograph of the flowers of the new cultivar. The color shown is a true as is reasonably possible to obtain by conventional photographic procedures. The colors of the various plant parts are defined by reference to The Royal Horticultural Society Colour Chart. Descriptions of colors in ordinary terms represented where appropriate for clarity in meaning.

The following is a detailed description of the new variety of *Liriope* based on observations made of plants grown in commercial nursery production practices at Rode Groundcovers, Inc. in Williston, Fla. The parentage is unknown to inventor. The average age of the plants observed was about 12 months.

DISTINCTIVE CHARACTERISTICS

| Characteristic | 'Love Potion #13' | 'Evergreen Giant' | 'Merton Jacobs' |
|---|---|---|---|
| Height (Mature) | 18–24" | 24–30" | 24–30" |
| Width (Mature) | 24–30" | 24–30" | 24–30" |
| Bloom Period | June–September | September–October | August–September |
| Raceme Length | 17–21" | 6–10" | 14–18" |
| Leaf Length | 18" | 21" | 18" |
| Leaf Width | ½" | 5/16" | ¼" |
| Leaf Color (Mature) | 137A | 137B | 143A |

Classification:
[Botanic] *Liriope muscari* 'Love Potion #13'.
Form—Dense, grass-like clump.

The plant normally grows at a rate of about 12" or more per year and reaches a height of about 18–24" and spread of 24–30" at maturity.

Foliage: A dense habit is formed from leaves arising from a central crown. The form of the leaf is simple, linear with an acute apex and cunate base with an entire margin. The texture of the leaf's surface is smooth, glossy and leathery. The grass-like, mature dark green leaves have a green color 137A on the upper side of the leaf which is glossy and glabrous. The underside is green 137B. The veins are green 137A and the area between the veins is 137C. The average number of leaves per stem is 23. The average length is 18 inches with a width of ½ inch. The plant is acaulescent and the leaves are basically equitant.

Inflorescence: The small profuse flowers grow in clusters of 6 and reducing to 2 at the apex. Typically, the diameter of the flower is 10 millimeters, while the depth is 3.5 millimeters. When first opening, the shape of the flower is a cup, later closing. The flowers form on a raceme scape which has an average length of about 24" with an average of 69 pedicels on each scape. The pedicels have a violet color of 80D. The bloom period is early and long, in Florida, starting in June and ending in September. The violet color of the open flower is 88A. The other edge of the flower petal has a violet color of 88D, wherein the petal itself has a purple-violet color 80D. There are 3 petals per flower and 3 petaloids. The petals have an entire margin and are polypetalous.

Flower buds: The small flower buds have a diameter of 3 millimeters and are of an ovoid form. The sepals are hooded over the bud and stand erect. There are six sepals having a color or 88C and a smooth texture. They are spear shaped. The unopened flower bud has a violet color of 88D. The bud has a smooth texture and no pubescence. The shape of the calyx is ovoid with a smooth aspect. The peduncle has a length of 4 to 7 millimeters, and is rigid. The peduncle typically has a diameter of about 1 millimeter, a smooth texture and a color of 76D. The flower buds on pedicles decrease in number from the base of the raceme to the apex, 6 to 2.

Reproductive Organs: The reproductive organs are bisexual, complete and perfect. There are six stamens, basifixed anthers in a connective arrangement. The length of the stamen is 1.5 millimeters and the width is 0.5 millimeters. The color is 6A. The filaments are 3 millimeters in length and the same color as the flower. The plant has on pistil which is 4 millimeters in length with color of 69B. The ovaries have a color of 69D. The ovaries are superior with 3 locules, 2 ovums per locule.

Fruit: The fruit resembles a berry, is globose 3/16" to 5/16" in diameter containing one or two seeds, ⅛"–¼" in diameter, having a color of 196A. The mature fruit has a green color 139A. The fruit rarely appears with an average of about 1 fruit per 200 plants.

Disease and pest resistance: The plant is insect and disease free with no chemical sprays at Williston, Fla. As observed [at Rode Groundcovers, Inc.] the cultivar has better resistance to *Phytopthora* spp *Fusarium oxysporum* and *Rhizoctonia solani* than other known *Liriope* varieties.

The plant has no above ground stems. It grows by adding small clumps of leaves on short rhizomes on the side of an existing clump. As the plant grows, the clump becomes larger. The plants are propagated by separating the clump. The plant material has differences with known *Liriope* varieties. The following tables show comparative information with the new variety and Evergreen giant and Merton Jacobs.

Comparison measurement of leaf blade length (measured ½" above soil line)

| 'Evergreen Giant' | | 'Love Potion #13' | | 'Merton Jacobs' |
|---|---|---|---|---|
| 21.06 inches | [Average] | 17.8 inches | [Average] | 18.2 inches |

Thirty specimens of each variety were used in this study. For each variety, the measurements were combined and averaged. The leaf blade length of this cultivar is slightly shorter than the Merton Jacobs, described in U.S. Plant Pat. No. 12,068 and is significantly shorter than the Evergreen giant.

| Comparison measurement of leaf blade width (measured at mid length of blade) width given in 16th inch | | | | |
|---|---|---|---|---|
| 'Evergreen Giant' | | 'Love Potion #13' | | 'Merton Jacobs' |
| 5/16 inches | [Rounded] | ½ inches | [Rounded] | ¼ inches |

Thirty plants of each variety were measured with the leaf blade width of the new cultivar on average being twice as wide as the Merton Jacobs variety and slightly wider than the parent stock, Evergreen giant.

| Foliage Color Comparison | | | |
|---|---|---|---|
| Plant Part | 'Evergreen Giant' RHC#/color group | 'Love potion #13' RHC#/color group | 'Merton Jacobs' pp#12068 RHC#/ color group |
| Upper side of leaf | 137B/green | 137A/green | 143A/green |
| Under side of leaf | 143A/green | 137B/green | 137C/green |
| Leaf veins | 143B/green | 137A/green | 137A/green |
| Leaf area between veins | 143C/green | 137C/green | 137D/green |

| Flower Color Comparison | | | |
|---|---|---|---|
| Plant Part | 'Evergreen Giant' RHC#/color group | 'Love Potion #13' RHC#/color group | 'Merton Jacobs' pp#12068 RHC#/ color group |
| Unopened flower bud | 85B/violet | 88D/violet | 85B/violet |
| Open flower | 82B/purple violet | 88A/violet | 85B/violet |
| Outer edge of flower petal | 82C/purple violet | 88D/violet | 82D/purple violet |
| Flower petal | 80D/purple violet | 80D/purple violet | 85D/violet |
| Immature flower buds | 160C/grey yellow | 86B/violet | 155C/white |
| Pollen | 6A/yellow | 5A/yellow | 3B/yellow |
| Raceme base | 79B/purple violet | 181C/grey red | 76D/purple |
| Raceme apex | 77A/purple | 62C/red purple | 76a/purple |
| Pedicel | 85C/violet | 80D/violet | 85D/violet |

The above Foliage and Flower Color Comparisons were observed on an August afternoon in Williston, Fla.

| Comparison of length of flower Raceme in inches (measured ½" above the soil line) | | | | |
|---|---|---|---|---|
| 'Evergreen Giant' | | 'Love Potion #13' | | 'Merton Jacobs' |
| 11.6 inches | Average | 16.3 inches | Average | 14 inches |

Ten plants of each variety were measured. 'Love Potion #13's flower raceme is approximately 30% longer than its parent stock, Evergreen giant, and 24% longer than Merton Jacobs U.S. Plant Pat. No. 12,068.

| Comparison of number of flower bundles per raceme | | | | |
|---|---|---|---|---|
| 'Evergreen Giant' | | 'Love Potion #13' | | 'Merton Jacobs' |
| 23.1 | Average | 55.9 | Average | 28.9 |

Ten plants of each variety were measured. 'Love Potion #13' has approximately twice the number of flower bundles as Evergreen giant or Merton Jacobs U.S. Plant Pat. No. 12,068. This strong distinction in floral display allows 'Love Potion #13' to provide much stronger bloom impact than other *Liriope* varieties on the market. 'Love Potion #13' has significantly more flowers, which open simultaneously. This increased quantity of flower bundles and individual flowers also allows for a longer duration of raceme color.

| Average number of leaves per division | | | | |
|---|---|---|---|---|
| 'Evergreen Giant' | | 'Love potion #13' | | 'Merton Jacobs' |
| 12 | [Rounded] | 23 | [Rounded] | 16 |

Ten plants of each variety were measured, 'Love Potion #13' has approximately two times as many leaves per division as Evergreen giant and 70% more than Merton Jacobs U.S. Plant Pat. No. 12,068.

| Comparison of fresh weight of 30 leaves | | |
|---|---|---|
| 'Evergreen Giant' | 'Love Potion #13' | 'Merton Jacobs' |
| 74 grams | 59 grams | 36 grams |

A wider leaf surface and a thinner leaf thickness make the new cultivar's fresh weight 63% heavier than Merton Jacobs and 25% lighter than Evergreen giant.

| Comparison of fresh weight of 10 flower Racemes | | |
|---|---|---|
| 'Evergreen Giant' | 'Love Potion #13' | 'Merton Jacobs' |
| 27 grams | 39 grams | 30 grams |

The density and quantity of the flower bundles when the flower racemes make the present cultivar 31% heavier than its parent stock, Evergreen giant and 25% heavier than the Merton Jacobs.

I claim:

1. A new and distinct variety of *Liriope* plant named 'Love Potion No. 13' as illustrated and described.

* * * * *